(12) United States Patent
Skyggebjerg et al.

(10) Patent No.: US 7,133,329 B2
(45) Date of Patent: Nov. 7, 2006

(54) DEVICE WITH TIME INDICATING MEANS

(75) Inventors: Ole Skyggebjerg, Soborg (DK); Lars Hofmann Christensen, Jyllinge (DK); Rasmus Panduro, Copenhagen (DK); Nina Bjorlig, Hellerup (DK); Steffen Lav, Bronshoj (DK); Barry Weben, Livermore, CA (US); Manuel Alvarez-Icaza, Inverness (GB); Steven Syme, Inverness (GB)

(73) Assignee: Novo Nordisk A/S, Bagsvaerd (DK)

( * ) Notice: Subject to any disclaimer, the term of this patent is extended or adjusted under 35 U.S.C. 154(b) by 350 days.

(21) Appl. No.: 10/618,878

(22) Filed: Jul. 14, 2003

(65) Prior Publication Data
US 2004/0062148 A1 Apr. 1, 2004

Related U.S. Application Data

(60) Provisional application No. 60/398,300, filed on Jul. 23, 2002.

(30) Foreign Application Priority Data
Aug. 19, 2002 (EP) .................................. 02388054

(51) Int. Cl.
*G04F 8/00* (2006.01)
*G04F 10/00* (2006.01)
(52) U.S. Cl. ........................ 368/113; 368/10; 368/107
(58) Field of Classification Search ................ 368/10, 368/107, 108, 113, 118, 120
See application file for complete search history.

(56) References Cited

U.S. PATENT DOCUMENTS

| | | | |
|---|---|---|---|
| 4,419,016 A * | 12/1983 | Zoltan | 368/10 |
| 4,939,705 A * | 7/1990 | Hamilton et al. | 368/10 |
| 5,233,571 A * | 8/1993 | Wirtschafter | 368/10 |
| 5,598,567 A | 1/1997 | Ninomiya | 395/750 |
| 6,248,090 B1 | 6/2001 | Jensen et al. | 604/67 |
| 6,302,855 B1 * | 10/2001 | Lav et al. | 600/584 |
| 6,529,446 B1 * | 3/2003 | de la Huerga | 368/10 |
| 6,667,936 B1 * | 12/2003 | Ditzig | 368/10 |
| 6,845,064 B1 * | 1/2005 | Hildebrandt | 368/10 |

FOREIGN PATENT DOCUMENTS

| | | |
|---|---|---|
| DE | 3824217 A1 | 1/1990 |
| EP | 0 087 491 | 9/1983 |
| FR | 2 820 311 | 1/2002 |

* cited by examiner

*Primary Examiner*—Andrew H. Hirshfeld
*Assistant Examiner*—Leo T. Hinze
(74) *Attorney, Agent, or Firm*—Marc A. Began; Reza Green; Richard W. Bork

(57) ABSTRACT

The invention relates to a timer device capable of performing one or more control actions in response to the time lapsed since a user initiated action took place. The timer device comprises contact means operatable between two conditions, timer means, and means for storing first and second time stamps. The device further comprises control means for setting a first time stamp in response to the contact means being operated between first and second conditions, setting a second time stamp in response to the contact means being operated between the second and first conditions, calculating the time elapsed between the two time stamps, comparing the elapsed time with a preset time value, and performing a control action if the elapsed time is greater than the preset time value.

8 Claims, 8 Drawing Sheets

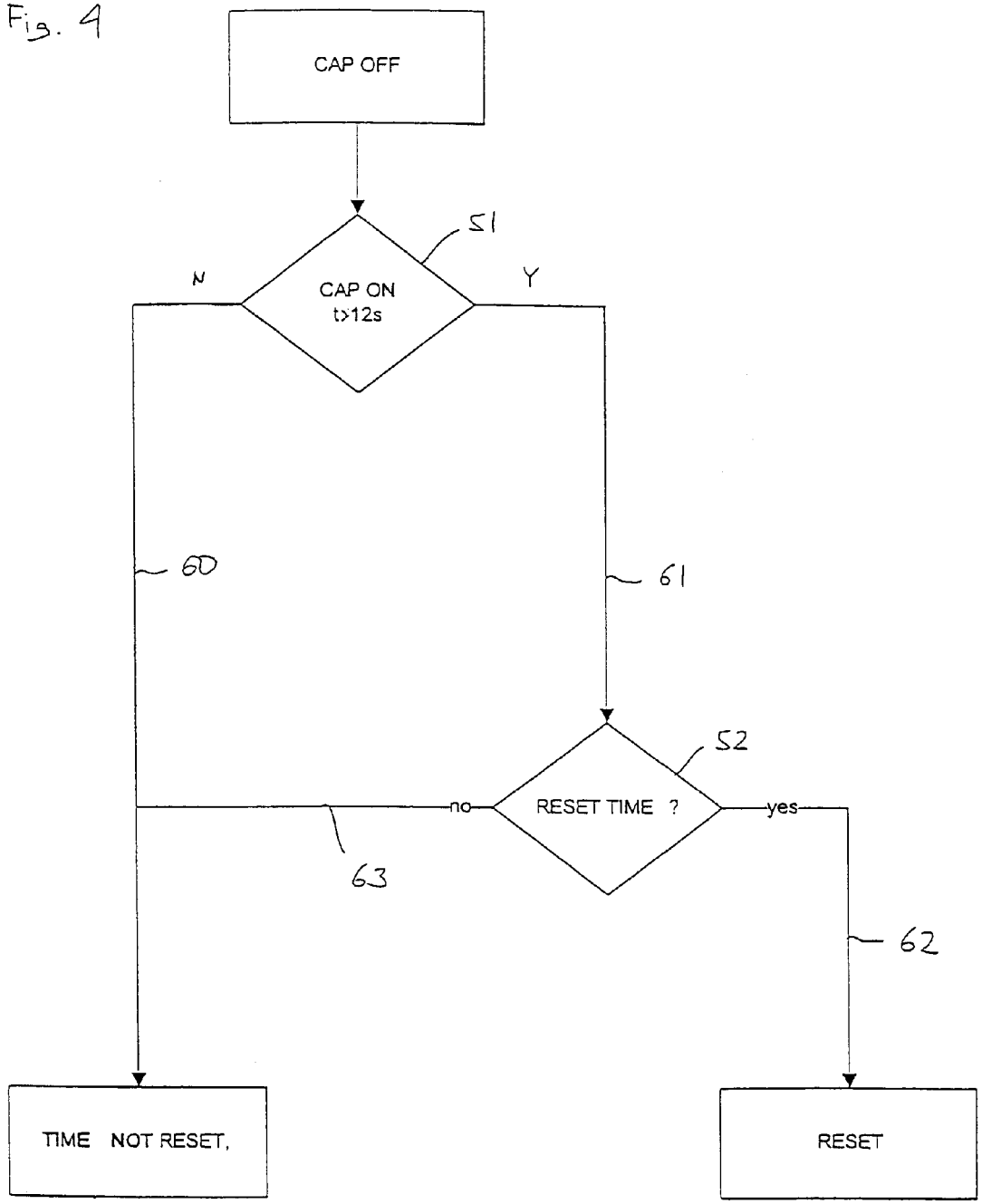

000# DEVICE WITH TIME INDICATING MEANS

CROSS REFERENCE TO RELATED APPLICATIONS

This application claims priority under 35 U.S.C. 119 of European application no. EP 02388054.5 filed Aug. 19, 2002 and U.S. provisional application No. 60/398,300 filed Jul. 23, 2002, the contents of both are fully incorporated herein by reference.

FIELD OF THE INVENTION

The present invention relates to an indicator device capable of performing one or more control actions in response to the time lapsed since a user initiated action took place. In exemplary embodiments the indicator device is adapted to engage a device capable of performing a user initiated action, especially a medical injection device adapted to deliver a given amount of an active substance such as insulin to the user.

BACKGROUND OF THE INVENTION

To patients, such as diabetics, who have to frequently inject themselves with a drug, it is necessary to keep account of when an injection has to be made or when an injection last time took place. This information could be in the form either of exact time information, e.g. the next injection should take place at 5h00 or the last injection took place at 3h00, or the information may be provided as a dynamic timer or stop watch function, e.g. the next injection should take place in 3h45 or the last injection took place for 2h30.

A number of devices have been described which may provide a patient with useful information when using such devices for the injection of a drug such as insulin a number of times over the day.

EP 87 491 (Günter Petz) discloses a kit comprising a storage box for insulin vials and a syringe, the kit being provided with a timer device by which the time for the latest injection may be set manually. Further the hour for the next injection may be set and the timing device may function as an alarm clock sounding an alarm when it is time for this next injection. However, in a world where people in a short time may cross between different time zones, and the hours in the time zones even may shift from summer to winter time, a reference to the hour may be uncertain. Here the count down is more adequate but has the drawback that unless you are ready to take an injection immediately when the alarm sounds you will have a new time account to handle, e.g. for how long an interval was the alarm set and how long time has passed from the sound of the alarm till the injection is actually made. EP 87 491 is hereby incorporated by reference.

DE 38 24 217 (Pavel Hančl) discloses an injection device comprising timer and control means coupled to the injection actuation means, i.e. the exact time for each actuation of the device, and thus normally for an injection, is automatically captured by the timer and control means and stored in a memory. For each actuation (injection) performed the amount of drug infused is memorized together with a time stamp as in a log book, e.g. 5 units of a given insulin were infused at 4:38. The device is adapted for memorizing a number of such log book datasets which then can be recalled by the patient or any attendant medical staff person. The device may also be operated to indicate the time lapsed since the individual earlier injections took place. In addition to these features, DE 38 24 217 also discloses timer, stop watch and alarm means as known from EP 87 491. DE 38 24 217 is hereby incorporated by reference.

U.S. Pat. No. 6,248,090 (assigned to Novo Nordisk A/S) discloses an injection device having a dose setting mechanism, a button operable to carry out an injection movement to inject the set dose, a switch operated at the start or at the completion of the injection, or at a time between the start and the completion of the injection, the switch operating electronic timer means. In the disclosed embodiment the amount of the last dose is stored and a stop watch is reset and started when the switch is operated, the device comprising means for displaying to the user the time lapsed since the last reset, for example in pictogram form displaying one or more segments each representing a given amount of time. In this way, the stop watch counts the time passed (e.g. the number of full hours, each hour represented by a segment shown in a LCD display) from the latest operation of the switch, i.e. from the latest actuation (injection) performed, whereby the user may have a comprehensive view of the time which has passed after the latest injection and the size of this last injection. In this way the user is able to set the next dose with regard to these parameters. U.S. Pat. No. 6,248,090, is hereby incorporated by reference.

As appears from the above, devices have been described which provide the user with time information correlated to a specific injection action which has been performed by the user. In these devices the dose setting and injection mechanism are formed integrally with the electronic control, clock and display means necessary for providing the desired information, this resulting in a relatively expensive device most suited for use as a re-useable or durable device, e.g. a device which can be refilled with a drug such as a prefilled cartridge.

However, many users prefer to use prefilled, disposable injection devices such as the Flex Pen™ manufactured and sold by Novo Nordisk A/S. As such disposable devices have to be manufactured cost-effectively, the incorporation of electronic control and display means are normally dispensed with.

It would thus be desirable if users of disposable (or simple) devices could be provided with the same functionality as offered by more expensive (normally durable) devices, e.g. time indicator means providing information as to when the last actuation of a drug delivery device took place, which actuation normally would be associated with an injection performed by the user.

DISCLOSURE OF THE INVENTION

The present invention is based on the realisation that a high degree of user friendliness can be provided by a durable control device adapted to be connected to a disposable device, wherein the durable device makes assumptions and/or proposals based on simple registrations performed when the two devices are connected to or disconnected from each other. In this regard, the disposable device merely serves as a contact actuating means for these registrations.

In the above as well as in the following, reference will be made to drug injection devices, especially for insulin, however, the present invention may be used in any other technical field in which similar situations of use give rise to similar problems.

In a first aspect the present invention is based on the concept that the amount of time lapsed from the registration of an event is indicative of what has happened. Correspondingly, a device may be provided with control means which will "take decisions" or "ask questions" in accordance with time registrations made.

More specifically, in accordance with the first aspect of the invention, a timer device is provided comprising contact means which can be operated between a first condition and a second condition, time means, means for storing a first time stamp, a second time stamp, and a first time-period value, control means adapted for setting a first time stamp in response to the contact means being operated between the first condition and the second condition, setting a second time stamp in response to the contact means being operated between the second condition and the first condition, calculating the time elapsed between the first and second time stamp, comparing the elapsed time with the first time-period value, and performing a first control action if the elapsed time is greater than the first time-period value.

The time means will typically be a quartz controlled clock device provided integrally with the controlling means in the form of a single integrated circuit (IC) which also comprises ROM memory for storing an executing program instructions as well as RAM memory for storing the different time stamps. The time means is preferably operating as a normal real time clock, the time stamps being stored as points of time, however, the first time stamp may also be set to "zero" with the second time stamp directly indicating the time lapsed from the first time stamp. The contact means may be in the form of simple on/off means such that the first condition represents an "on" state and the second condition represents an "off" state, e.g. the "on" state may represent that two device portions are assembled in a given way and the "off" state may represent that two device portions are separated from each other. The contact means may also be in the form of a system wherein two individual contacts are used to operate the contact means between the first condition and second condition.

As stated, the control means will perform a control action in case the first time condition is met, i.e. a given time has elapsed. This control action may be any desirable action, such as resetting and starting a stop watch, setting a time stamp, transmitting information or performing a function such as sounding an alarm.

As discussed above, the action performed is based on events actually taking place, e.g. that two device portions are taken apart for a given time and a corresponding action is performed (or not performed) by the user such as an injection of a medicament. In case the two device portions are taken apart for only a very short time, e.g. accidentally or when "playing" with the device, it is assumed that no action is performed by the user and correspondingly no control action will take place. On the other hand, in case the two device portions are taken apart for a longer period of time, it is assumed that an action is performed by the user and correspondingly the control action will take place, however, in case no action is performed by the user, the timer device preferably comprises first actuation means for cancelling the first control action. As appears, when a third time stamp is stored, this may be regarded as the point of time for the last injection performed by the user, whereas to first and second time stamps are used to decide whether or not a control action should be performed. Advantageously, the timer device is provided with display means for displaying one or more time stamps and/or for indicating the time lapsed since the third time stamp.

In a preferred embodiment the timer device further comprises means for storing a second time-period value, the control means being further adapted for comparing the elapsed time with the second time-period value, and performing a second control action if the elapsed time is greater than the second time-period value.

By this additional feature, the timer device can be adapted to properly identify an "unusual" state, for example in case that the above-described two device portions are taken apart for a "long" period of time indicating that the two portions accidentally have separated (e.g. when carried in a bag or pocket) or that the user has taken the two portions apart to prepare an injection but has been disturbed (e.g. by the phone) with or without performing the planned action. In this case the second control action may be in the form of actuating an alarm to alert the user of the "unusual" condition or to set a time flag in accordance with a predefined regimen.

Preferably the timer device further comprises first actuation means for cancelling or confirming the second control action, as well as second actuation means, such that the second control action replaces the third time stamp with the second time stamp or, in response to actuation of the second actuation means, with the first time stamp, or vice versa.

By these additional features, the user may either cancel any control action whereby the timer device is reset to the state before the last separation took place, e.g. before the two portions accidentally separated in the pocket, or the user may "toggle" the device to indicate that an action (such as a medicament injection) actually took place as the two portions were separated (after which the user for example went to the phone without reattaching the two portions) or an action took place just prior to reattaching the two portions (as the user ended a telephone conversation and resumed the action initiated when the telephone rang).

In case confirmation is required using the first actuation means, the second actuation means may be used to toggle between different time stamps which may then need to be confirmed before the device is reset.

Whereas the above-described embodiments have relied on the principle of calculating the time elapsed between first and second time stamps, this providing a basis for a number of different actions to be formed as outlined above, it is also possible to implement the basic concept of the present invention using the principle used e.g. with keyboards or simple contacts to prevent double-actuation, i.e. "bounce".

More specifically, for such an alternative a timer device is provided comprising contact means operatable between a first condition and a second condition, timer means, means for storing a time-period value, and control means adapted for: starting a timer in response to the contact means being operated between the first condition and the second condition, stopping and resetting the timer in response to the contact means being operated between the second condition and the first condition before the timer has reached the time-period value, or performing a first control action when the timer has reached the time-period value.

In preferred embodiments the timer device is incorporated in a device for use by a patient for medical self treatment, comprising a first device portion for performing an operation such as an injection of a medicament, a second device portion comprising the above-described timer device, wherein the first and second device portions have mutually cooperating coupling means for detachably assembling the first and second device portions to form a single portable unit, the contact means being operated between the first condition and the second condition when the first and second device portions are detached from each other, and the contact means being operated between the second condition and the first condition when the first and second device portions are attached to each other.

In a further preferred embodiment the first device portion comprises a reservoir (for) containing a medicament, the reservoir comprising a distal end portion adapted to engage an injection needle providing fluid communication with the interior of the reservoir, dose setting means allowing the user to set a desired dose of medicament to be injected, and driving means for expelling medicament from the reservoir in accordance with the set dose, the second device portion being in the form of a cap adapted to cover the distal end portion when the first and second device portions are attached to each other.

As it is an object of the present invention to provide a timer device adapted to be used in combination with a disposable device (such as a disposable, prefilled medicament injection device), it is contemplated that the timer device is offered as an optional piece of equipment which is adapted to be used in combination with a given disposable device.

Therefore, in a further preferred embodiment a cap is provided having an open end and a cap interior adapted to receive a medical device, the cap comprising a timer device as described above, wherein the contact means can be operated between the first condition and the second condition when the cap and the medical device are removed from each other, and the contact means can be operated between the second condition and the first condition when the medical device are received in the cap interior.

As appears, a functional feature of the above-defined cap relies on the cooperation with a device which does not form part of this aspect of the present invention, however, it is submitted that the skilled person will readily be able to identify contact means adapted for the stated function.

Advantageously, the timer device may be combined with or formed integrally with one or more additional electronic devices, this allowing components such as electronic control and storage means, display means and actuation means to be shared. In a specifically preferred embodiment, a body fluid analyzer is provided in combination with the timer device, e.g. a blood glucose monitor (BGM) device.

In a second aspect of the present invention, a system for use by a patient for medical self treatment is provided, comprising a user operatable device portion for performing an operation such as an injection of a medicament, and at least a first and a second cap, each of the caps and the user operatable device portion having mutually cooperating coupling means for detachably assembling the first and second device portions to form a single portable unit, wherein the first cap comprises the above-described timer device, the contact means being operated when the first cap and user operatable device portions are detached from and reattached to each other.

In a preferred embodiment the second cap and/or the user operatable device portion comprises no electronic means, e.g. the latter components are sold as a disposable unit with the first cap comprising the timer device being provided as an optional durable cap.

As also appears from the above disclosure of the invention, when in the context of the present application the term "timer device" is used, it merely indicates that a functionality is provided which is based on time, i.e. the timing function may be in the form of one or more recorded points of time or a timer counting up or down from a point of time, e.g. as a stopwatch. When it is described that a given time stamp is replaced with another time stamp, this is meant to include "derivatives" of this other time stamp, e.g. for a given reason it may be desirable to add or subtract an amount of time before a time stamp is replaced.

As used herein, the term "drug" or "medicament" is meant to encompass any drug-containing flowable medicament capable of being passed through a delivery means such as a hollow needle in a controlled manner, such as a liquid, solution, gel or fine suspension. There is essentially no limitation on the type of liquid drug which can be used with the invention other than to exclude those liquid drugs which would be inappropriate to deliver to the subject in an auto-mated fashion using the infusion device of the invention. Representative drugs include peptides, proteins, and hormones. In the description of the preferred embodiments reference will be made to the use of insulin. Correspondingly, the term "subcutaneous" infusion is meant to encompass any method of infusion into a subject.

BRIEF DESCRIPTION OF THE DRAWINGS

In the following the invention will be further described with references to the drawings, wherein FIG. 4 shows a first flow-chart illustrating three situations of use.

DESCRIPTION OF THE PREFERRED EMBODIMENTS

Figure 1A:
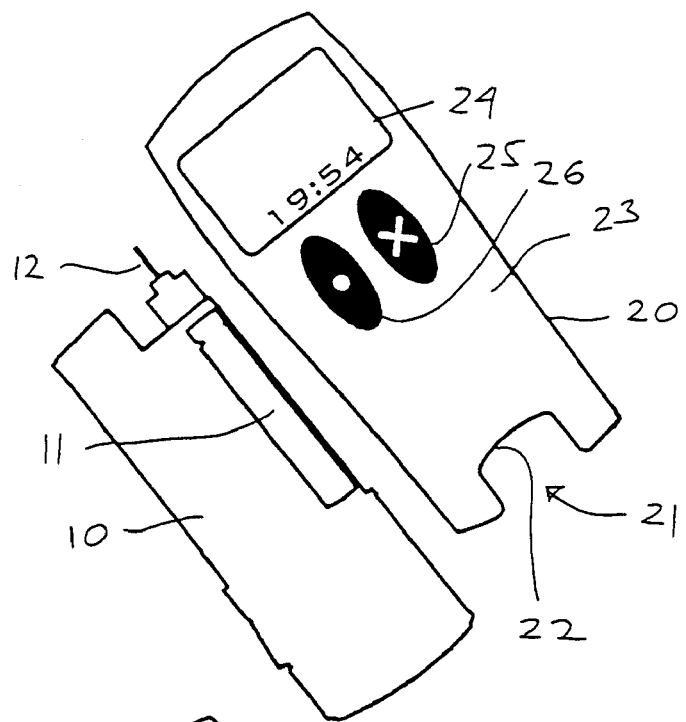
FIGS. 1A–1C show an embodiment of the invention corresponding to a first situation of use.

FIG. 1A shows an injection device for use by a patient for medical self treatment, such a device also being known as a "pen" or a "doser" device.

The injection device comprises a first device portion 10 in the form of a "doser" for performing a subcutaneous injection of a medicament and a second device portion 20 in the form of a cap configured to be attached on the doser. The doser comprises a reservoir 11 containing a medicament, a distal end of the reservoir being provided with an injection needle 12 providing fluid communication with the interior of the reservoir, a dose setting mechanism (not shown) allowing the user to set a desired dose the medicament to be injected, and driving means (e.g. a push button, not shown) for expelling medicament from the reservoir in accordance with the set dose.

The cap comprises an interior space with a distal opening 21 allowing the doser to be received there within (see FIG. 1B), the distally facing rim portion defining the opening into the interior space comprising a cut-out portion allowing the doser to be gripped and thus pulled out. The cap comprises a user oriented surface 23 provided with a LCD display 24 and first and second actuation means 25, 26. The display comprises first display means 27 for displaying a first point of time, second display means 28 for displaying a second point of time, as well as third display means 29 for displaying further information (to be discussed in detail below).

The cap and the doser are provided with mutually cooperating coupling means for detachably assembling the two device portions to form a single portable unit. The cap comprises contact means which is operated between a first condition and a second condition when the first and second device portions are detached from each other, and which are operated between the second condition and the first condition when the first and second device portions are attached to each other. In the shown embodiment the contact means is arranged in the cap cavity and actuated by a surface portion of the doser. The contact means may be of any desired nature such as a micro-switch or based on opto- or magneto-electronic means. Preferably the contact means are operated just as the doser is withdrawn or inserted into the cap interior.

Figure 8:
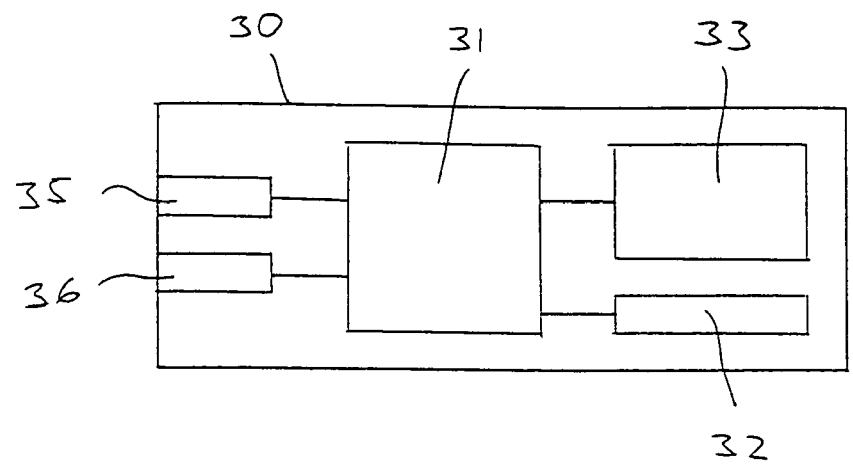
FIG. 8 shows a schematic representation of a timer device.

The cap further comprises a number of micro-electronic components for performing the desired functions. As shown schematically in FIG. 8, a carrier 30 is provided with a processing and control unit 31 which also performs the timer and clock functions, a memory 32, a display 33 as well an energy source (not shown). Input to the processing and control unit is provided through contact means 35 (e.g. a micro-switch) and actuator means 36 (e.g. one or more user operatable buttons).

Figure 1B:
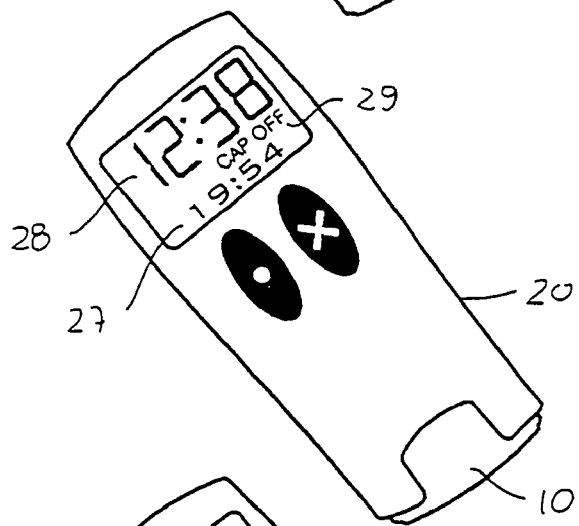
Figure 1C:
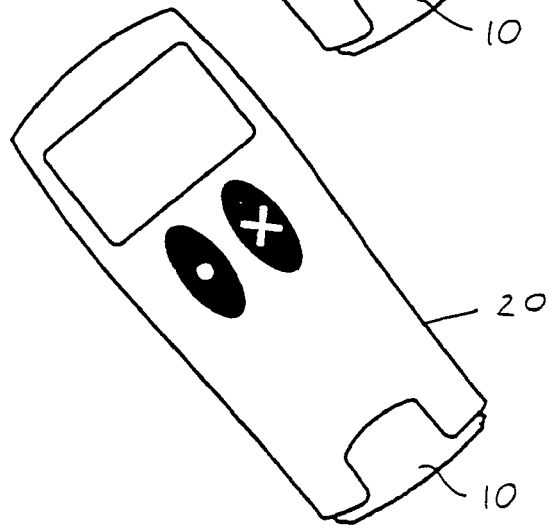

With reference to FIGS. 1A–1C a first situation of use will be described. When the doser 10 is removed from the cap 20, the current time is shown by the first display means (FIG. 1A). When the doser is reinserted before a given period of time (e.g. 12 seconds) has lapsed corresponding to a first time-period value stored in the memory 32, the last user time stamp is shown by the second display means. The user time stamp (which internally may be represented as a third time stamp as described in the introductory portion) corresponds to the point of time at which the last injection was deemed to have been performed, i.e. the last time the cap was taken off for "injection purposes" as indicated by the "CAP OFF" sign. After a given timeout period (e.g. 30 seconds) the display turns off. In summary, the first situation of use corresponds to a situation in which the user after a short period of time regrets having taken the cap off or when the user is just playing with the cap, e.g. like playing with the in-out mechanism of a ball pen.

Figure 2A:
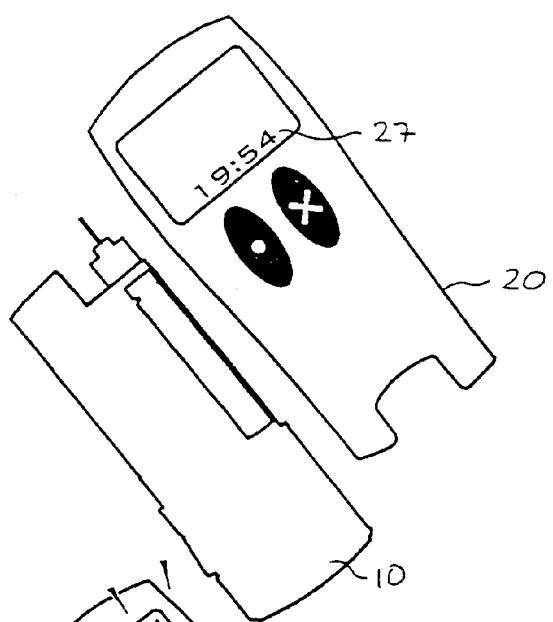
FIGS. 2A–2D show an embodiment of the invention corresponding to a second situation of use.
Figure 2B:
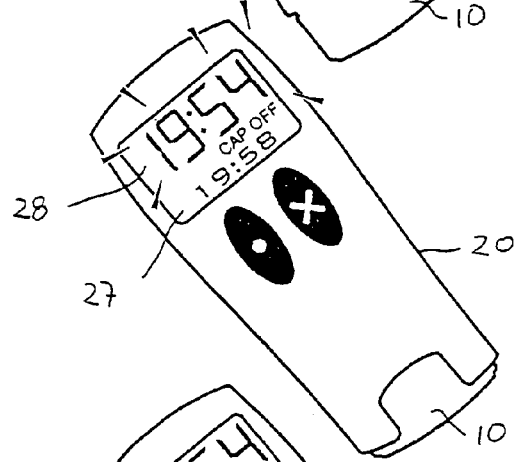
Figure 2C:
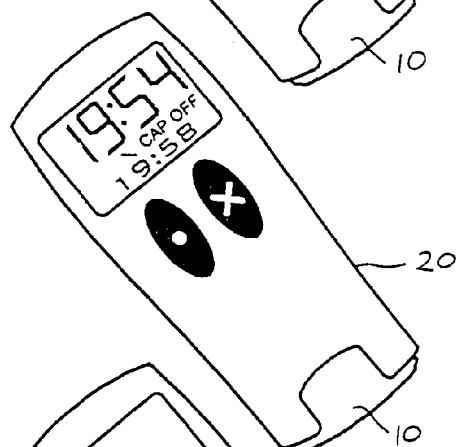
Figure 2D:
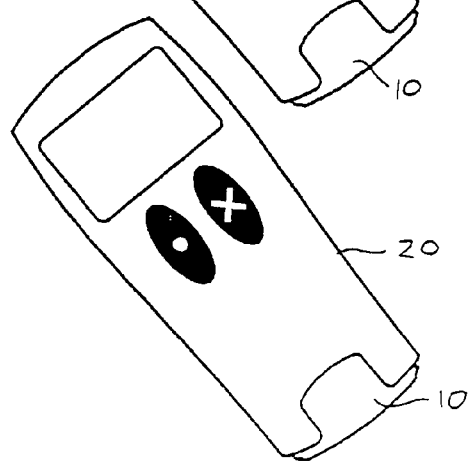

With reference to FIGS. 2A–2D a second situation of use will be described. When the doser 10 is removed from the cap 20, the current time is shown by the first display means 27 (FIG. 2A). When the doser is reinserted after a given period of time (e.g. 4 minutes and thereby longer than the 12 seconds corresponding to the first time-period value), it is assumed that an injection of medicament has taken place, this resulting in the second display means 28 showing the point of time (19:54) at which the cap was taken off. As appears, the first display means shows the running time. To indicate that the user time stamp will be reset automatically, the second display means flashes (FIG. 2B) for a certain period of time (e.g. 15 seconds) after which it stops flashing indicating that the user time stamp has been reset (FIG. 2C). After a given timeout period (e.g. 30 seconds) the display turns off. In summary, the second situation of use corresponds to the "normal" situation in which the user has taken the cap off for a couple of minutes for performing an injection.

Figure 3A:
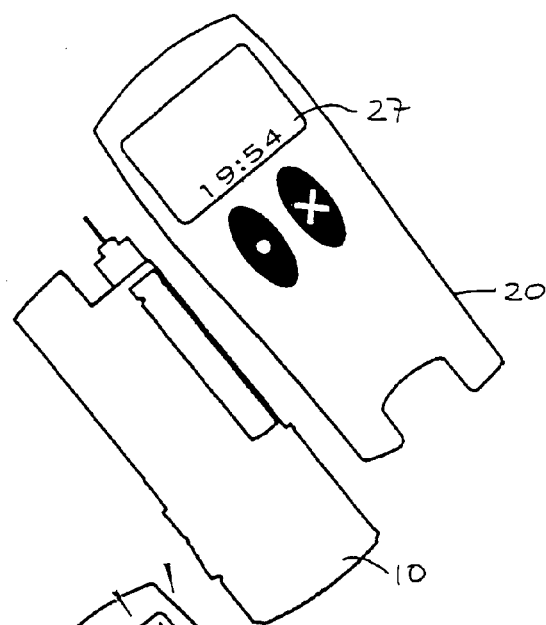
FIGS. 3A–3D show an embodiment of the invention corresponding to a third situation of use.
Figure 3B:
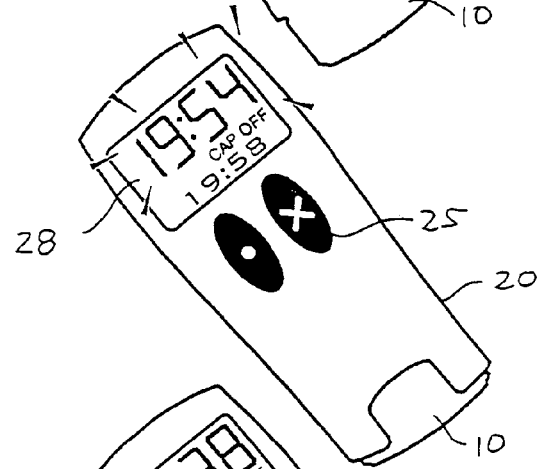
Figure 3C:
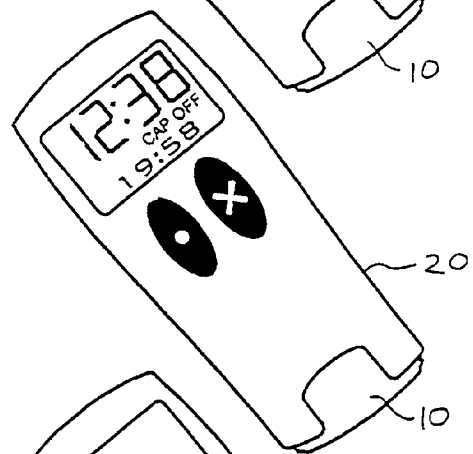
Figure 3D:
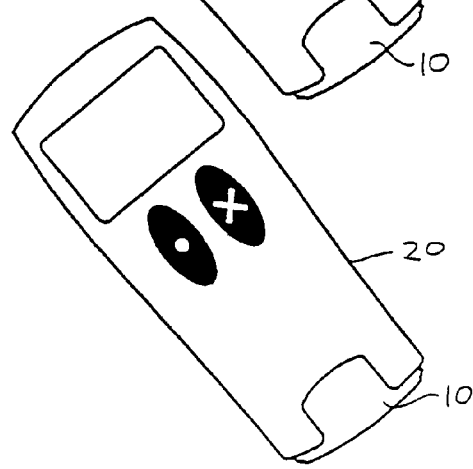

With reference to FIGS. 3A–3D a third situation of use will be described. When the doser 10 is removed from the cap 20, the current time is again shown by the first display means 27 (FIG. 3A). When the doser is reinserted after a given period of time (e.g. 4 minutes and thereby longer than the 12 seconds corresponding to the first time-period value), it is assumed that an injection of medicament has taken place, this resulting in the second means 28 showing the point of time (19:54) at which the cap was taken off. To indicate that the user time stamp will be reset automatically, the second display means flashes (FIG. 2B) for a certain period of time (e.g. 15 seconds). However, in case that no injection has taken place (e.g. the user has misplaced the new needle to be mounted), the user can cancel the reset action by pressing a "cancel" button 25, i.e. the first actuation means, which results in the last user time stamp appearing in the display (FIG. 2C). After a given timeout period (e.g. 30 seconds) the display turns off. In summary, the third situation of use corresponds to a "stop" situation in which the user for some reason did not finish the initiated injection action.

In order to prevent any insulin overdosing and thereby running the risk of hypoglycaemia, the above-described timer device is set-up to assume that an injection has taken place if it was actually possible, i.e. the cap was off for more than 12 seconds. As cancellation of the automatic reset action requires a positive action by the user, the risk of overdosing is reduced.

However, in case underdosing is to be prevented, which may be the case in treatment with e.g. growth hormone (GH), the timer device may be set up to assume that an injection has not taken place although it was actually possible, i.e. the cap was off for more than 12 seconds. The display may still be flashing the reset time, however, in this case a reset action requires a positive "confirm" action by the user, otherwise the timer may not be reset, and the user time stamp will remain 12:38, whereby the risk of underdosing is reduced.

The above-described three situations of use can be summarized by the diagram shown in FIG. 4, the diagram showing two "actions", a first action 51 taken by the timer device in accordance with the "12 second" time value, and a second action 52 of resetting or cancellation taken by the timer device respectively the user. As appears, the first situation of use corresponds to the path 60, the second situation of use corresponds to the path 61, 62 and the third situation of use corresponds to the path 61, 63.

Next, two further situations of use will be described corresponding to an embodiment of the invention comprising means for storing a second time-period value, and where the control means is further adapted for comparing the elapsed time with the second time-period value and cooperate with the second actuation means.

Figure 5A:
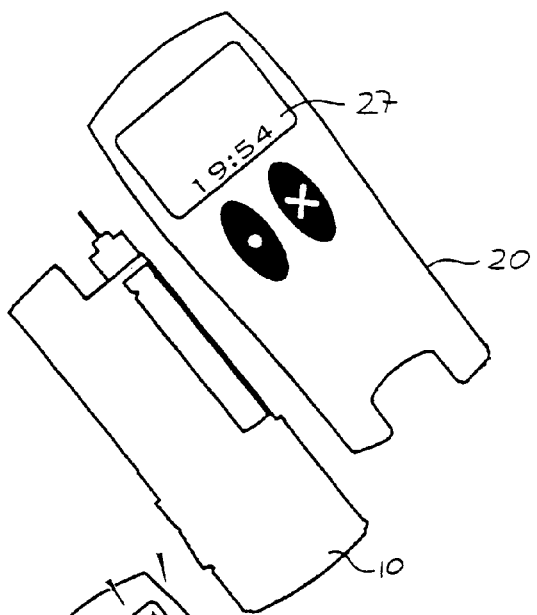
FIGS. 5A–5D show an embodiment of the invention corresponding to fourth and fifth situations of use.
Figure 5C:
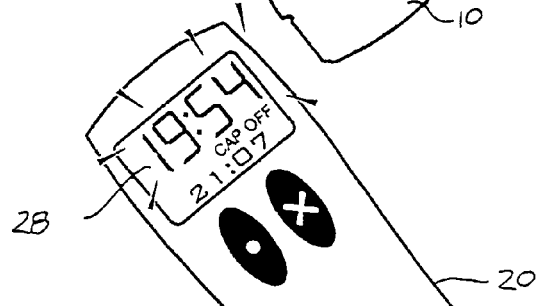

With reference to FIGS. 5A–5D a fourth situation of use will be described. When the doser 10 is removed from the cap 20, the current time is shown by the first display means 27 (FIG. 5A). When the doser is reinserted after a relatively long period of time (e.g. 73 minutes and thereby longer than the 30 minutes corresponding to a second time-period value), it is assumed that an injection of medicament has taken place just prior to the doser was reinserted, this resulting in the second display means 28 showing the point of time (21:07) at which the cap was put on as indicated by the "CAP ON" sign. To indicate that the user time stamp will be reset automatically, the second display means flashes (FIG. 2B) for a certain period of time (e.g. 15 seconds). However, in case the injection took place just after the cap was taken off (for example, in case the user was distracted by a phone call and forgot to reinsert the doser), corresponding to a fifth situation of use, the user can toggle the reset action by pressing the "selector" button 26, i.e. the second actuation means, which results in the 19:54 "CAP OFF" time stamp appearing in the display (FIG. 5C). After a given timeout period (e.g. 30 seconds) the display turns off. In summary, the fourth situation of use corresponds to a "forgot" situation in which the user for some reason did leave the cap of for a relatively long time but performed an injection either at the beginning or end of the cap-off period.

Figure 5B:
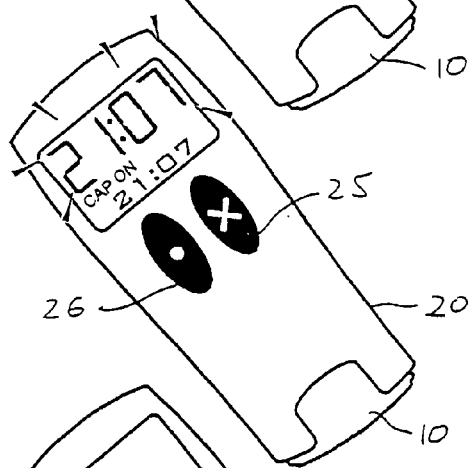
Figure 5D:
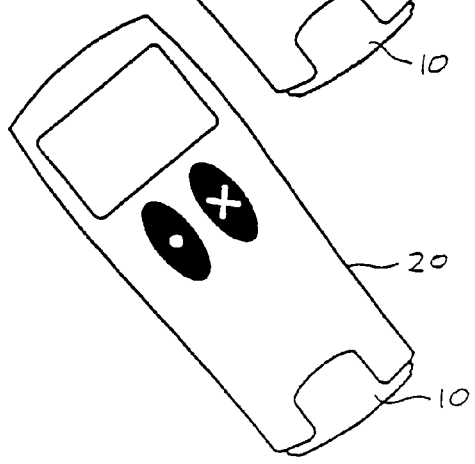

In case that no injection has taken place in the situation of FIG. 5B and corresponding to a sixth situation of use (e.g. cap has fallen of when the device was carried in a bag), the user can cancel the reset action by pressing the "cancel" button 25, i.e. the first actuation means, which results in the last user time stamp appearing in the display, e.g. a situation in which the current time would be 21:07 shown by the first display means and the user time stamp would be 12:38 shown by the second display means. In summary, the third situation of use corresponds to a "fallen off" situation in which the user finds the cap separated from the doser.

In order to prevent any overdosing and thereby running the risk of hypoglycaemia, the above-described timer device is set-up to assume that an injection has taken place as late as possible, i.e. when the doser was inserted in the cap after 73 minutes. As cancellation or toggle of the automatic reset action requires a positive action by the user, the risk of overdosing is reduced.

However, in case underdosing is to be prevented, which may be the case in treatment with e.g. growth hormone (GH), the timer device may be set up to assume that an injection has (i) not taken place although it was actually possible, or (ii) primarily assume that an injection has taken place as early as possible, i.e. when the doser was removed from the cap 73 minutes ago. The display may still be flashing the 21:07 "cap-on" reset time, however, in this case a reset action requires a positive "confirm" action by the user, otherwise the timer may not be reset and the user time stamp will remain 12:38. In case an injection took place when the cap was taken off, the user may actuate the selector button which will result in a flashing 19.54 which may then be confirmed. In this way the risk of underdosing is reduced.

Figure 6:
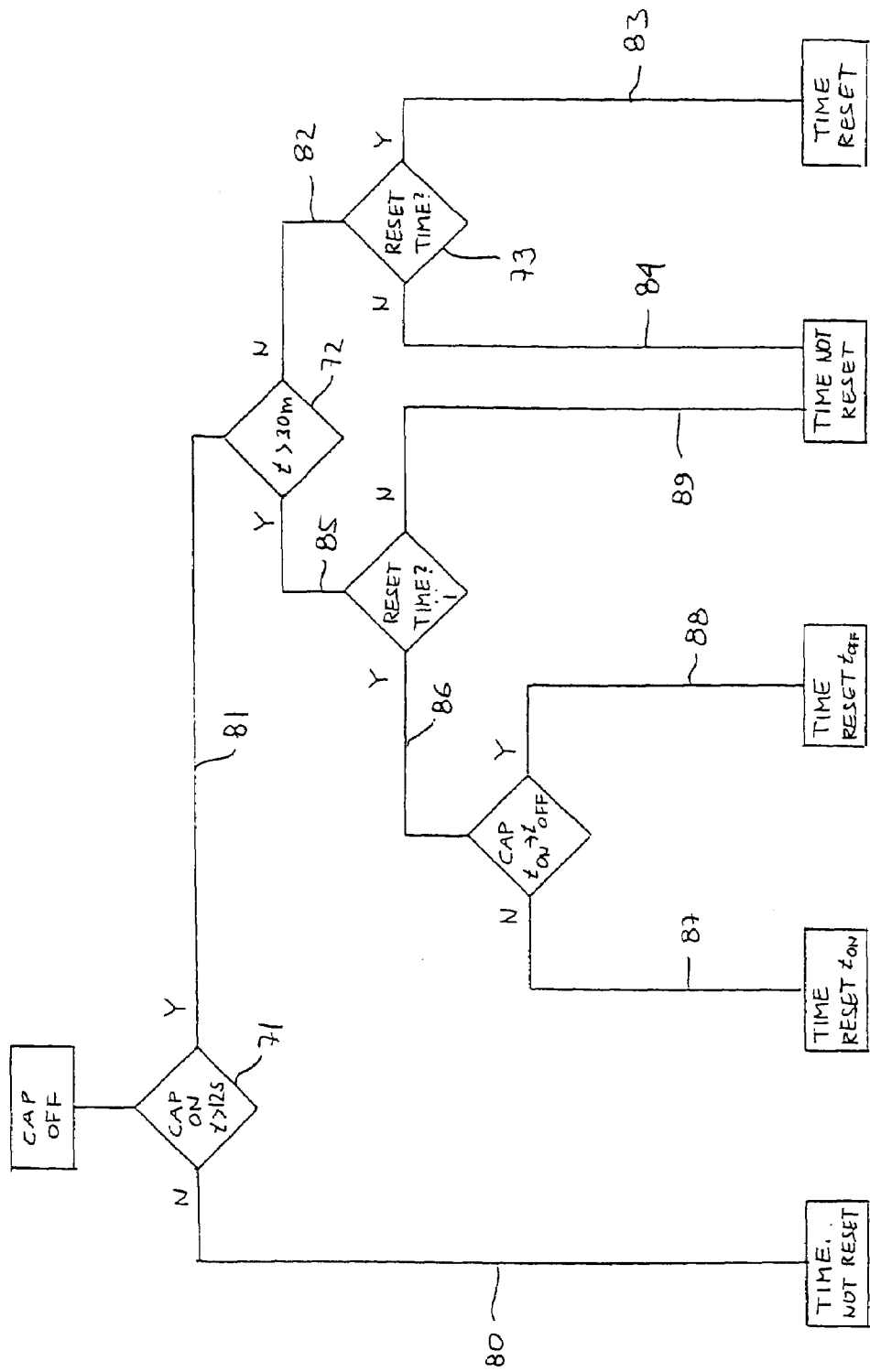
FIG. 6 shows a second flow-chart illustrating six situations of use.

The above-described six situations of use can be summarized by the diagram shown in FIG. 6, the diagram showing five "actions": a first action 71 taken by the timer device in accordance with the "12 second" time value, a second action 72 taken by the timer device in accordance with the "30 minutes" time value, a third action 73 of resetting or cancellation taken by the timer device respectively the user, a fourth action 74 of resetting or cancellation taken by the timer device respectively the user, and a fifth action 75 of resetting in accordance with the cap-on or the cap-off time.

As appears, the first situation of use corresponds to the path 80, the second situation of use corresponds to the path 81, 82, 83, the third situation of use corresponds to the path 81, 82, 84, the fourth situation of use corresponds to the path 81, 85, 86, 87, the fifth situation of use corresponds to the path 81, 85, 86, 88 and the sixth situation of use corresponds to the path 81, 85, 89.

Figure 7:
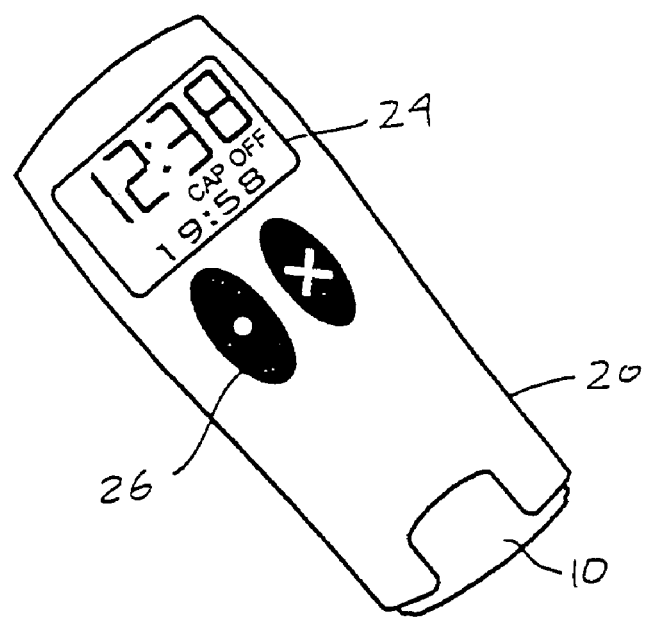
FIG. 7 shows a further situation of use using an embodiment of the present invention.

As shown in FIG. 7, when the selector button 26 is activated when the cap 20 is mounted on the doser 10, the display 24 is activated and the actual user time stamp is displayed, i.e. the time for the last injection.

Many modifications of the above described embodiments would be possible within the scope of invention as defined in the accompanying claims. For example, the first and second actuation means may be provided by a single button, a short actuation resulting in a first type of actuation and a longer sustained actuation resulting in a second type of actuation. Instead of displaying a "point of time" user time stamp, the time elapsed since this time stamp could be placed in a "stop watch fashion" either in the form of a real time clock or by graphically displaying segments as disclosed in U.S. Pat. No. 6,248,090. To further enhance the "intelligence" of the timer device, additional time-period values may be used predict events taking place. The control means may be pre-programmed or may be user programmable, e.g. allowing the user to set the time-period values, just as the memory means may be adopted to store a number of recent time stamp values (e.g. the user time stamp) which may also be associated with a date stamp.

In the above description of the preferred embodiments, the different structures providing mechanical and electrical contact and communication between the different components just as the means providing the described functionality for the different components (i.e. dose setting, reservoir, energy source, memory, control means, display etc.) have been described to a degree to which the concept of the present invention will be apparent to the skilled reader. The detailed construction and specification for the different structures are considered the object of a normal design procedure performed by the skilled person along the lines set out in the present specification.

We claim:

1. A timer device, comprising:
    contact means (35) operatable between a first condition and a second condition,
    timer means (31),
    means (32) for storing a first time stamp, a second time stamp, and a first time-period value,
    control means (31) adapted for:
        setting a first time stamp in response to the contact means being operated between the first condition and the second condition,
        setting a second time stamp in response to the contact means being operated between the second condition and the first condition,
        calculating the time elapsed between the first and second time stamps,
        comparing the elapsed time with the first time-period value, and
        performing a first control action if the elapsed time is greater than the first time-period value;
    means (32) for storing a second time-period value, and wherein the control means is further adapted for:
        comparing the elapsed time with the second time-period value, and
        performing a second control action if the elapsed time is greater than the second time-period value and further comprising:
    first actuation means (25) for cancelling the second control action, and
    second actuation means (26), and wherein the second control action replaces a third time stamp with the second time stamp or, in response to actuation of the second actuation means, with the first time stamp.

2. A timer device as defined in claim 1, further comprising:
    first actuation means (25) for confirming the second control action, whereby no confirmation will cancel the second control action, and
    second actuation means (26), and wherein the second control action replaces the third time stamp with the second time stamp or, in response to actuation of the second actuation means, with the first time stamp.

3. A timer device as defined in claim 1, further comprising:
- first actuation means (25) for confirming the second control action, whereby no confirmation will cancel the second control action, and
- second actuation means (26), and wherein the second control action replaces the third time stamp with the first time stamp or, in response to actuation of the second actuation means, with the second time stamp.

4. A cap (20) having an open end and an interior space adapted to receive a medical device, the medical device comprising means for administering a preset dose of a drug to the patient, the cap comprising a timer device as defined in claim 3, wherein the contact means can be operated between the first condition and the second condition when the cap and the medical device are removed from each other, and the contact means can be operated between the second condition and the first condition when the medical device are received in the cap interior.

5. A timer device as defined in claim 1, further comprising:
- display means (33, 27, 28, 29) for displaying one or more time stamps and/or for indicating the time lapsed since the third time stamp.

6. A device use by a patient for medical self treatment, further comprising:
- a first device portion (10) for performing an operation,
- a second device portion (20) comprising a timer device as defined in claim 1,
- wherein the first and second device portions have mutually cooperating coupling means for detachably assembling the first and second device portions to form a single portable unit, the contact means being operated between the first condition and the second condition when the first and second device portions are detached from each other, and the contact means being operated between the second condition and the first condition when the first and second device portions are attached to each other.

7. A device as defined in claim 6, wherein the first device portion comprises means for administering a preset dose of a drug to the patient.

8. A device as defined in claim 7, wherein the first device portion further comprises a distal end portion at which an infusion needle is or can be mounted, and the second device portion is in the form of a cap adapted to cover the distal end portion when the first and second device portions are attached to each other, the cap preferably comprising a body fluid analyzer.

* * * * *